(12) United States Patent
Csikós et al.

(10) Patent No.: US 7,619,082 B2
(45) Date of Patent: Nov. 17, 2009

(54) PROCESS FOR THE PREPARATION OF 3-SPIRO'CYCLOHEXAN-1,3'-'3H!INDOLIN-2'-ONE! DERIVATIVES

(75) Inventors: Eva Csikós, Budapest (HU); Csaba Gönczi, Budapest (HU); Felix Hajdú, Budapest (HU); István Hermecz, Budapest (HU); Gergely Héja, Szentendre (HU); Gergelyné Héja, Szentendre (HU); Csilla Majláth, Budapest (HU); Lajos Nagy, Szentendre (HU); Andrea Sántáné Csutor, Budapest (HU); Tiborné Szomor, Budapest (HU); Györgyné Szvoboda, Dunakeszi (HU)

(73) Assignee: sanofi-aventis, Paris (FR)

( * ) Notice: Subject to any disclaimer, the term of this patent is extended or adjusted under 35 U.S.C. 154(b) by 523 days.

(21) Appl. No.: 10/485,133

(22) PCT Filed: Jul. 25, 2002

(86) PCT No.: PCT/HU02/00075

§ 371 (c)(1),
(2), (4) Date: Jun. 7, 2004

(87) PCT Pub. No.: WO03/011827

PCT Pub. Date: Feb. 13, 2003

(65) Prior Publication Data

US 2004/0225124 A1 Nov. 11, 2004

(30) Foreign Application Priority Data

Jul. 31, 2001 (HU) .................................. 0103122
Jul. 4, 2002 (HU) .................................. 0202193

(51) Int. Cl.
*C07D 273/01* (2006.01)
(52) U.S. Cl. .................................................. 544/70
(58) Field of Classification Search .................. 544/70
See application file for complete search history.

(56) References Cited

U.S. PATENT DOCUMENTS

| 6,046,341 | A | 4/2000 | Foulon et al. |
| 6,548,702 | B1 * | 4/2003 | Gonczi et al. ............... 564/142 |
| 6,600,039 | B1 * | 7/2003 | Heja et al. ..................... 544/70 |

FOREIGN PATENT DOCUMENTS

| WO | WO 97/15556 | 5/1997 |
| WO | WO 01/05791 | 1/2001 |

OTHER PUBLICATIONS

H. Venkatesan et al., The Journal of Organic Chemistry, vol. 66, No. 11, pp. 3653-3661(2001).

IIIi, Synthesis, No. 2, p. 136 (1979).
Jones, K., et al., Chiral Induction in Aryl Radical Cyclisations, Tetrahedron Letters, vol. 30, No. 20, 2657-2660, 1989.
Sleboka-Tilt, et al., O Exchange Accompanying the Basic Hydrolysis of Primary, Secondary, and Tertiary Toluamides. 2. The Importance of Amine Leaving Abilities from the Anionic Tetrahedral Intermediates, J. Am. Chem. Soc., vol. 112, No. 23; 1990; 8507-8514.
Ohgawara, Phase Transfer Catalyst, Ghoseishiyaku, Khodansha (1980), pp. 188-189 (with English translation).
Rao et al., Synthesis and Reactions of 2-Bis(methylthio)methylene-1-methyl-3-oxoindole: A Facile Access to Benzo- and Heterocyclo-Fused Carbazoles and Indoles, Tetrahedron 55 (1999), pp. 11563-11578.
Phase Transfer Catalyst, Shokubaikouza, Khodansha (1986), Chapter 8, vol. 10. pp. 164-165 (with English translation).

\* cited by examiner

*Primary Examiner*—James O Wilson
*Assistant Examiner*—Ebenezer Sackey
(74) *Attorney, Agent, or Firm*—Brian R. Morrill

(57) ABSTRACT

The invention relates to a process for the preparation of a compound of the formula (I) by reacting a compound of the formula (II) with a compound of the formula (III) characterized by dissolving the compounds of the formula (II) and formula (III) in a water-inmiscible organic solvent in the presence of a phase transfer catalyst, reacting with a.) an aqeuos solution of a base, or b.) a base in solid form directly and if desired transforming the compound of formula (I) thus obtained into its salt.

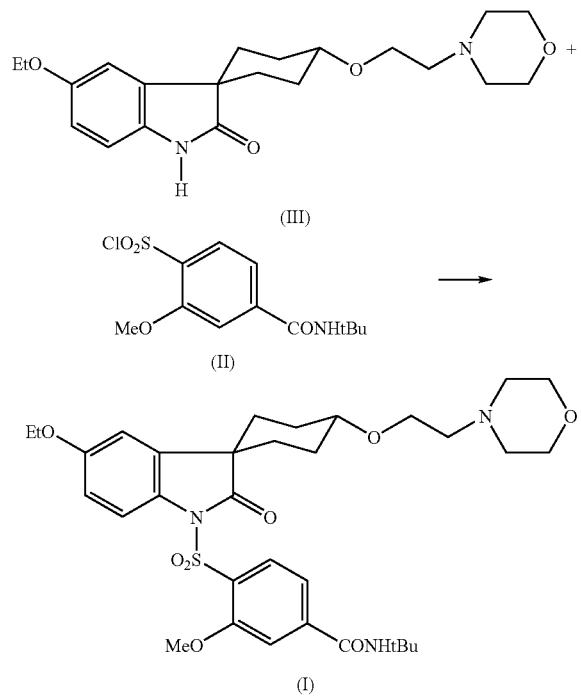

18 Claims, 1 Drawing Sheet

Figure 1:
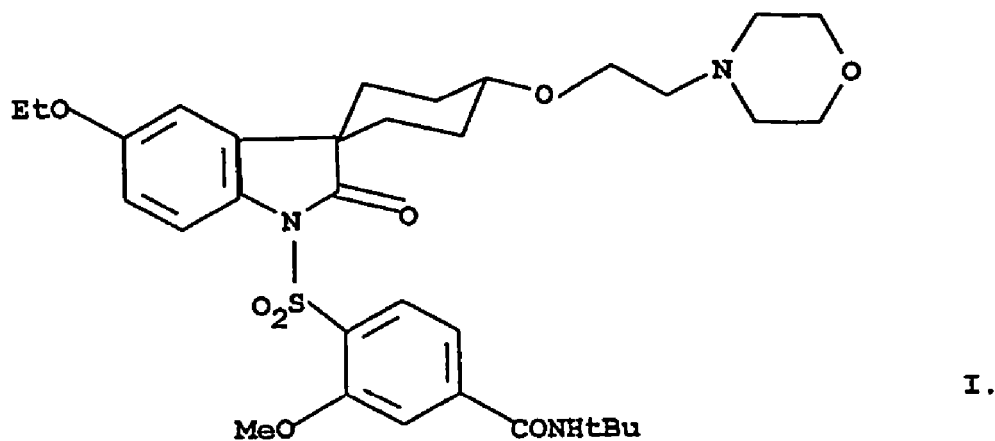

I.

II.

III.

PROCESS FOR THE PREPARATION OF 3-SPIRO'CYCLOHEXAN-1,3'-'3H!INDOLIN-2'-ONE! DERIVATIVES

The subject of the invention is a new process for the preparation of N-(1,1-dimethylethyl)-4-[[5'-ethoxy-4-cis-[2-(4-morpholino)ethoxy]-2'-oxospiro[cyclohexan-1,3'-[3H]indol]-1'(2'H)-yl]-sulfonyl]-3-methoxy-benzamide of formula (I) and of its salts, having vasopressin $V_2$ antagonistic effect.

According to WO 97/15556 the compound of formula (I) was synthesized by reacting the spiro/cis-4-(beta-morpholinoethyloxy)cyclohexan-1,3'-(5'-ethoxy)-[3H]indol-2'[1'H]-one of formula (II) with the 2-methoxy-4-(N-t-butylaminocarbonyl)benzene sulfochloride of formula (III), by using potassium-t-butylate in tetrahydrofuran.

Due to the applied solvent (tetrahydrofuran) and temperature (between −60° C. and −40° C.) industrial realization of the process would encounter difficulties, in addition the yield of the reaction is low, the product obtained is contaminated, it needs repeated crystallisations to purify it.

Practically the same process is described by Venkatesan et. al. (*J. Org. Chem.* 2001, 66, 3653-3661, on page 3661.).

According to WO-01/05791 the sulfonylation is carried out in water-free medium, in dimethyl sulfoxide at room temperature, with excellent yield.

This finding brought about a great technical achievement, since the quality of the product allowed to leave out all further purification steps, compared with the process described in WO97/15556, page 39. Preparation 11 and *J. Org. Chem.* 2001, 66, 3653-3661, Experimental Part, page 3661.

In industrial scale, however, the use of dimethyl sulfoxide is not desirable, our aim was therefore to work out a process without using this solvent.

We have found, to our surprise, that the spiro/cis-4-(beta-morpholinoethyloxy)-cyclohexan-1,3'-(5'-ethoxy)-[3H]indol-2'[1'H]-one, compound of formula (II), which has a high pK value, i.e. which behaves as a very weak acid, or is rather a molecule with amphoteric character, can be sulfonylated with the compound of formula (III) on the nitrogen atom of the carboxamide group in the presence of a base, working in a two-phase system and using a suitable phase transfer catalyst. That discovery opened the possibility to prepare the compound of formula (I)—which is sensitive to hydrolysis—according to the present invention.

N-acylation of indole in the presence of phase transfer catalyst has already been described in the literature (V. O. Illi et al: Synthesises. 1979 page 136, and A. S. Bourlot et al: Synthesis 1994 page 411). Preparation of indolin-on type compounds, which are much less nucleophilic than indole, is not described in the above literatures, there is not even given a hint for their peparation.

Lack of knowledge on N-acylation of indolinones was the reason why the special methods described in applications WO-97/15556, WO01/05791 and in the publication in J. Org. Chem. have been worked out.

In the process according to the invention the compounds of formulae (II) and (III) are dissolved in a water-inmiscible organic solvent in the presence of a phase transfer catalyst, and reacted by adding to them a.) the aqueous solution of a base, or b.) a base in solid form directly to obtain the compound of formula (I), which—if desired—can be transformed into one of its salt.

The organic solvents can be first of all halogenated carbohydrates, advantageously dichloromethane, dichloroethane, trichloroethylene or chloroform, most preferably dichloromethane.

For phase-transfer catalysts, quaternary nitrogen containing compounds, preferably benzyl triethyl ammonium chloride, tetrabutyl ammonium hydrogen sulphate, cetyl pyridinium bromide, tetramethyl ammonium chloride, tetramethyl ammonium fluoride can be applied, but other types of phase transfer catalysts, for instance crown ethers can also be used.

As aqueous solution of a base according to process variant a.) most preferably aqueous sodium hydroxide or potassium hydroxide solutions can be used, in excesses of 1-5 equivalents, counted for the compound of the formula (II), in concentrations of 10% -50%, most preferably 4 equivalents of the base, in 30% solution are used.

According to process variant b.) the base used in solid form directly is most probably sodium-hydroxide or potassium-hydroxide, preferably in pellet form.

The reaction is carried out at a temperature between 5-40° C., preferably at 20-30° C.

Preferred stirring speed is 100-800 rotation/minute, most preferably 300 rotation/minute.

Compound of formula (III) is used in an excess of 0%-20%.

The process according to process variant a.) of our invention, in accordance with the aim, does not need water-free solvents and hard to ensure "dry" industrial equipments. Neither process variant a.) nor process variant b.) requires the use of alcoholates or metal hydrides. At the end of the reaction—in given case—, after separating the phases, the solvent can simply be regenerated. The processes of our invention are simple and environment friendly, they have all the advantages of the known sulfoxide method, but at the same time avoid the use of dimethyl sulfoxide, thus achieving the goal which was set.

Figure 2:
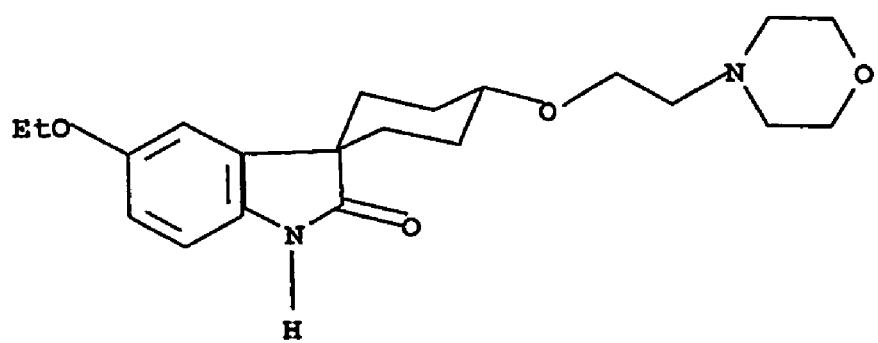
Figure 3:
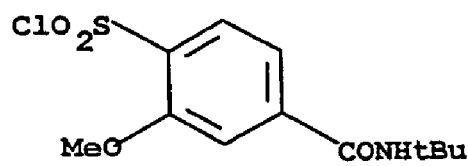

FIGS. 1, 2 and 3 show formula (I), (II) and (III).

Further details of our process are demonstrated in the following examples, without limiting the claims to the examples.

EXAMPLES

Example 1

37.47 g of spiro[cis-4-(β-morpholinoethyloxy)cyclohexan-1,3'-(5'-ethoxy)-[3H]indol]-2'[1'H]-one are dissolved in 200 cm³ of dichloromethane and to the solution 4-(N-tert-butylaminocarbonyl)-2-methoxybenzenesulfonyl chloride and 2 g of benzyl triethyl ammonium chloride are added at 20° C.

12 g of potassium hydroxide are dissolved in 40 cm³ of distilled water, and added to the above solution. The reaction mixture is stirred at 25-30° C. (stirring speed 500 r.p.m). The end point of the reaction is checked by thin layer chromatography. Reaction time is 2-2.5 hours. The phases are then separated, the organic phase is washed with water and dried. Dichloromethane is distilled out, the white crystalline residue, which contains the desired compound (I), is suspended in alcohol, and to the suspension 11.4 g of 85% phosphoric acid is added at 75° C. The solution is clarified by charcoal, filtered, the precipitating crystals are collected, washed with alcohol, and dried. 63.8 g of cis-N-(1,1-dimethylethyl)-4-[[5'-ethoxy4-[2-(4-morpholinyl)ethoxy]-2'-oxospiro[cyclohexane-1,3'-[3H]indol]-1'(2'H)-yl]sulfonyl]-3-methoxybenzamide phosphate monohydrate are obtained.

M.p.: 164° C.

Purity of the product is 99.5% (by HPLC), it can be used for the preparation of a drug product without further purification, phase transfer catalyst does not contaminate the product.

Examples 2-6

The process described in Example 1. is followed, by using the base and catalyst as given in the table below.

| | concentration of aqueous KOH | catalyst | | 1, in the form of base) | (%) |
|---|---|---|---|---|---|
| 2. | 1.8 eq. 23% | Benzyl triethylammonium chloride | 10% | 2 hours 88% | 96.50 |
| 3. | 1.8 eq. 10% | Tetrabutyl ammonium hydrogen sulfate | 10% | 5 hours 52% | 99.28 |
| 4. | 1.8 eq. 10% | Cetyl pyridinium bromide | 10% | 5 hours 71% | 98.80 |
| 5. | 1.8 eq. 10% | Tetramethylammonium chloride | 10% | 5 hours 68% | 97.50 |
| 6. | 1.8 eq. 10% | Tetramethylammonium fluoride | 10% | 5 hours 61% | 96.00 |

Example 7

28.08 g (0.075 Mol) of (spiro[cis-4-(β-morpholinoethyloxy)cyclohexane-1,3'-(5'-ethoxy)-[3H]indol]-2'[1'H]-one) and 27.52 g (0.09 Mol) of (4-(N-tert-butylaminocarbonyl)-2-methoxybenzenesulfonyl chloride and 1.71 g of benzyltriethylammonium chloride were solved in 150 ccm dichloromethane at 25° C. with stirring. (189 rpm) 5.46 g (0.136 Mol) of sodium-hydroxide were solved in 8.2 ccm ion free water and the solution was added to the above mentioned solution at 5° C. The temperature of the two-phase mixture was kept on 5-15° C. for 1.5 hours. Than the mixture was heated to reflux temperature, and kept it for 2 hours. Cooled back to 30° C., diluted with 100 ccm dichloromethane and 120 ccm tap water. After a short time the phases were separated. The organic layer was washed with 2×100 ccm water The dichloromethane was distilled off. 100 ccm 96% ethanol were added to the white crystalline and kept on the distillation. Stirred for 2 hours at 20° C. filtered off washed with 2×40 ccm ethanol (be suspended ) and dried.

42.6 g (88.2%) Mp.: 217-218° C. of cis-N-(1,1-dimethylethyl)-4-[[5'-ethoxy-4-[2-(4-morpholinyl)ethoxy]-2'-oxospiro[cyclohexane-1,3'-[3H]indol]-1'(2'H)-yl]sulfonyl]-3-methoxybenzamide were obtained.

Example 8

37.45 g (0.1 Mol) of spiro[cis-4-(β-morpholinoethyloxy)cyclohexane-1,3'-(5'-ethoxy)-[3H]indol]-2'[1'H]-one)- and 40.7 g (0.133 Mol) of (4-(N-tert-butylaminocarbonyl)-2-methoxybenzenesulfonyl chloride and 2.3 g of benzyltriethylammonium chloride were solved in 200 ccm dichloromethane at 25° C. with stirring (rpm: 150-200). 7.27 g (0.18 Mol) of sodium hydroxide pellet were added to it in one portion and kept the temperature at 30-35° C. The inorganic salt was filtered off washed with 2×20 ccm dichloromethane and the solvent was distilled till the solid phase appears. 100 ccm ethanol poured on it and kept on the distillation in atmospheric pressure The dichloromethane was removed. 100 ccm water was added to the thick, white suspension and stirred it for 1-1.5 hour in room temperature. Filtered off washed with water (3×50 ccm) and dried. 57-61 g (88-95%) of cis-N-(1,1-dimethylethyl)-4-[[5'-ethoxy-4-[2-(4-morpholinyl)ethoxy]-2'-oxospiro[cyclohexane-1,3'-[3H]indol]-1'(2'H)-yl]sulfonyl]-3-methoxybenzamide were obtained. Mp.: 216-218° C. 98.5-99% by HPLC.

What we claim is:

1. A process for preparing a compound of formula (I)

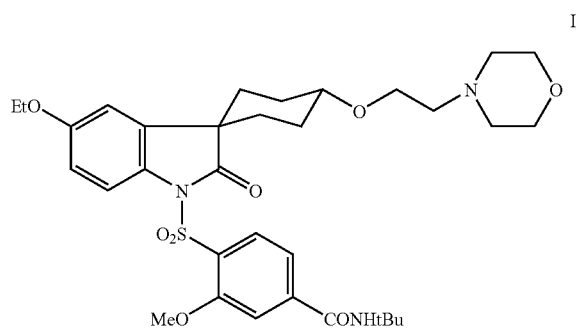

comprising dissolving a compound of formula (II)

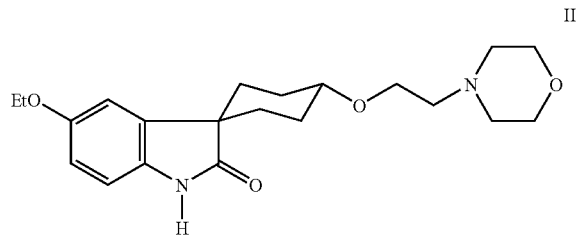

and a compound of formula (III)

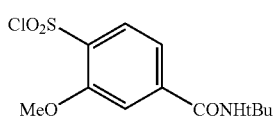

in a water immiscible organic solvent in the presence of a phase transfer catalyst, and then reacting with an aqueous solution of a base, or a base in solid form directly.

2. A process preparing a compound of formula (I)

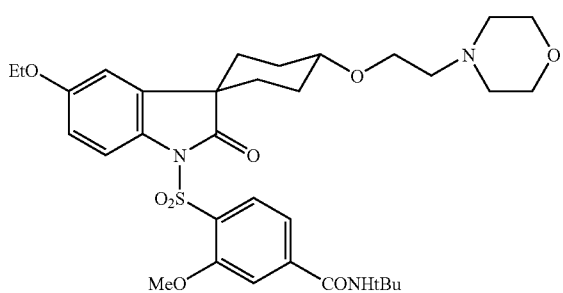

comprising dissolving a compound of formula (II)

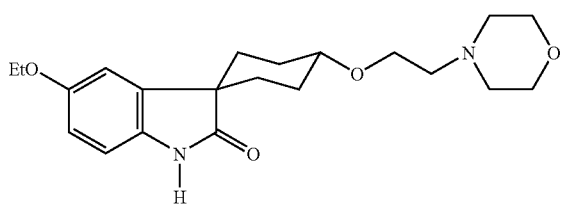

and a compound of formula (III)

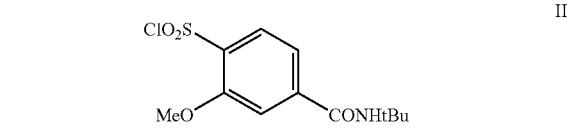

in a water immiscible organic solvent in the presence of a phase transfer catalyst, and then reacting with an aqueous solution of a base.

3. The process according to claim 1 wherein the organic solvent is halogenated carbohydrates.

4. The process according to claim 2 wherein the organic solvent is halogenated carbohydrates.

5. The process according to claim 1 wherein the phase transfer catalyst is a quaternary nitrogen atom containing phase transfer catalyst.

6. The process according to claim 2 wherein the phase transfer catalyst is a quaternary nitrogen atom containing phase transfer catalyst.

7. The process according to claim 1 wherein the base is sodium hydroxide or potassium hydroxide.

8. The process according to claim 2 wherein the aqueous solution of a base is an aqueous sodium hydroxide solution or aqueous potassium hydroxide solution.

9. The process according to claim 1 wherein the reaction is carried out at a temperature from 5° C. to 40° C.

10. The process according to claim 2 wherein the reaction is carried out at a temperature from 10° C. to 40° C.

11. The process according to claim 1 wherein the reaction is carried out by mixing at a speed of rotation of 100-800 r.p.m.

12. The process according to claim 2 wherein the reaction is carried out by mixing at a speed of rotation of 200-800 r.p.m.

13. The process according to claims 3 wherein the organic solvent is methylene chloride, ethylene chloride, trichloroethylene or chloroform.

14. The process according to claim 4 wherein the organic solvent is methylene chloride, cthylene chloride, trichloroethylene or chloroform.

15. The process according to claim 5 wherein the phase transfer catalyst is benzyl triethyl ammonium chloride, tetrabutyl ammonium hydrogen sulfate, cetyl pyridinium bromide, tetramethyl ammonium chloride, or tetramethyl ammonium fluoride.

16. The process according to claim 6 wherein the phase transfer catalyst is benzyl triethyl ammonium chloride, tetrabutyl ammonium hydrogen sulfate, cetyl pyridinium bromide, tetramethyl ammonium chloride, or tetramethyl ammonium fluoride.

17. The process according to claims 10 wherein the reaction is carried out at a temperature from 20° C. to 30° C.

18. The process according to claims 12 wherein the reaction is carried out at a speed of rotation of 300 r.p.m.

* * * * *